(12) United States Patent
Pilgrim

(10) Patent No.: US 10,456,170 B2
(45) Date of Patent: Oct. 29, 2019

(54) DEVICE FOR ENRICHING SPERMATOZOA

(71) Applicant: BluPink GmbH, Stuttgart (DE)

(72) Inventor: Thorsten Pilgrim, Gerlingen (DE)

(73) Assignee: BluPink GmbH, Stuttgart (DE)

( * ) Notice: Subject to any disclaimer, the term of this patent is extended or adjusted under 35 U.S.C. 154(b) by 291 days.

(21) Appl. No.: 15/022,124

(22) PCT Filed: Aug. 20, 2014

(86) PCT No.: PCT/EP2014/067772
§ 371 (c)(1),
(2) Date: Mar. 15, 2016

(87) PCT Pub. No.: WO2015/036214
PCT Pub. Date: Mar. 19, 2015

(65) Prior Publication Data
US 2016/0228150 A1    Aug. 11, 2016

(30) Foreign Application Priority Data
Sep. 16, 2013 (DE) .................. 10 2013 218 528

(51) Int. Cl.
*A61B 17/425* (2006.01)
*A61F 6/08* (2006.01)
*A61F 6/04* (2006.01)

(52) U.S. Cl.
CPC ............ *A61B 17/425* (2013.01); *A61F 6/08* (2013.01); *A61F 6/04* (2013.01)

(58) Field of Classification Search
CPC ............ A61B 17/425; A61F 6/04; A61F 6/08
See application file for complete search history.

(56) References Cited

U.S. PATENT DOCUMENTS

| 4,527,988 | A | 7/1985 | Lutz et al. |
| 5,640,973 | A | 6/1997 | Blinn |
| 7,371,517 | B2 | 5/2008 | Evans et al. |
| 8,138,319 | B2 | 3/2012 | Oksenberg et al. |
| 2003/0004556 | A1 | 1/2003 | McDaniel |
| 2007/0256691 | A1 | 11/2007 | Ogram et al. |
| 2011/0270127 | A1* | 11/2011 | Vered ............... A61B 10/0096 600/573 |

FOREIGN PATENT DOCUMENTS

| CN | 2045304 U | 10/1989 |
| DE | 44 34 320 A1 | 2/1995 |

(Continued)

OTHER PUBLICATIONS

International Search Report issued in connection with PCT/EP2014/067772.

(Continued)

*Primary Examiner* — Christine H Matthews
(74) *Attorney, Agent, or Firm* — Akerman LLP

(57) ABSTRACT

The invention relates to a device for insertion into a vaginal passage or for accommodation of a penis during coitus, comprising a selectively permeable separating wall for the enrichment of X-chromosome-bearing spermatozoa or Y-chromosome-bearing spermatozoa, wherein the separating wall shows an increased permeability for X-chromosome-bearing spermatozoa or Y-chromosome-bearing spermatozoa.

20 Claims, 2 Drawing Sheets

(56) References Cited

FOREIGN PATENT DOCUMENTS

Figure 1:
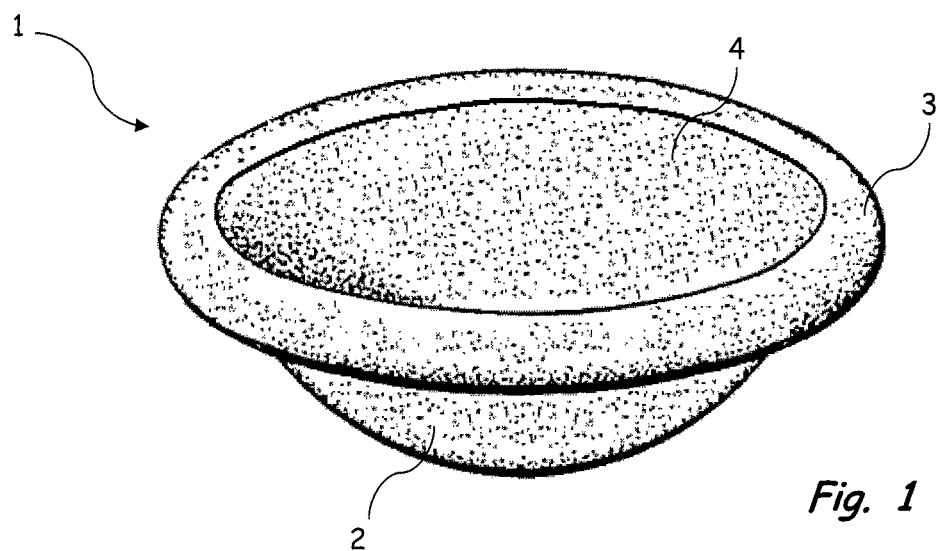

| WO | 02/052244 A2 | 7/2002 |
|---|---|---|
| WO | 03/086251 A1 | 10/2003 |
| WO | 2014/049620 A1 | 4/2014 |

OTHER PUBLICATIONS

German Search Report issued in connection with DE 10 2013 218 528.6.
Mehta et al., "Cause of Cessation of Viral Passage through Artificially-Induced Holes in Latex Condoms", Journal of Rubber Research, Jan. 1, 1998, pp. 1-13.
Office Action dated Apr. 5, 2018 in connection with corresponding Russian Application No. 2016113676/14(021427), English translation.
Cartwright et al., "Separation of bovine X and Y sperm based on surface differences," Molecular Reproduction and Development, Mar. 1993, 34(3), Abstract.
Gledhill, "Selection and separation of X- and Y-chromosome-bearing mammalian sperm," Gamete Res., Jul. 1988, 20(3), Abstract.
Cui, Kehui, "Size differences between human X and Y spermatozoa and prefertilization diagnosis", Molecular Human Reproduction, 1997, vol. 3(1)—(English translation of abstract enclosed).
Dzhakupov I.T. et al., "Fertility of cows and heifers when insemination of sexed sperm", Scientific notes UOVGAVM, 2011, vol. 47, Issue 2, Part 2—(English translation of abstract enclosed).
Office Action dated Aug. 10, 2018 issued in connection with corresponding Russian Patent Application No. 2016113676/14(021427), along with English translation of same.
Office Action dated Dec. 19, 2018 issued in connection with corresponding Chinese Patent Application No. 2201480062589.6, along with English translation of same.
Lixin, Luo, "The Latest Encyclopedia of Parenthood", Inner Mongolia People's Publishing House, Jan. 31, 2009, pp. 274-277.
Li Shunqiang, Chongqing, "Andrology", University Press, May 31, 1994.
Deng Xiaohui, Shandong, "Reproductive Medicine Technology and Its Colored Atlas", Science & Technology Press, Oct. 31, 2004.
Yinglu, Guo, et al., "Clinical Andrology", Hubei Science & Technology Press, Aug. 31, 1996.
Jiaming, Guo, et al., "Genetics", Progress of the Research on the Evaluation Methods of Isolation Purities of X-sorted Sperm and Y-sorted Sperm, vol. 30, Sep. 30, 2008.
Lei, Shi, et al., "Shanghai Journal of Animal Husbandry and Veterinary Medicine", Progress of the Research on the Gender Control Techniques of Isolation of X-sorted Sperm and Y-sorted Sperm, Dec. 31, 2007.

\* cited by examiner

DEVICE FOR ENRICHING SPERMATOZOA

This application is a national phase of PCT/EP2014/067772, filed Aug. 20, 2014, and claims priority to DE 10 2013 218 528.6, filed Sep. 16 2013, the entire contents of which are hereby incorporated by reference.

The invention relates to a device for insertion into a vaginal passage or for accommodation of a penis during coitus for the enrichment of spermatozoa.

Desire for being able to influence the birth sex of the descendants is probably as old as human history itself. Whereas for long terms in history especially male descendants were preferred, in a modern, industrialized world this seems to be of considerably subordinated relevance or even shifts in favour of female descendants.

Also for the purpose of a so-called family balancing, i.e. for creating a balance between sexes within the family, lots of couples desire the opportunity to at least increase the probability of procreating a descendant of specific sex.

In parts, desire for a sex is medically indicated, too. Particularly with regard to X-chromosomal-recessive hereditary diseases, there is the desire of being able to determine the descendants sex. Among this category of more than 500 diseases known till this day, are for example hemophilia, Duchenne muscular dystrophy as well as the Lesch-Nyhan syndrome. These diseases are caused by recessive genes on the X-chromosome, so that women as bearers of those genes need to reckon with their sons suffering from this specific disease with a probability of more than 50%.

Mammalian sperm generally contains approximately the same number of Y-chromosome-bearing spermatozoa (Y-spermatozoa) and X-chromosome-bearing spermatozoa (X-spermatozoa). The fertilisation of an egg cell by an Y-spermatozoon (also called Y-sperm or Y-spermatozoid) results in male descendants. The fertilisation by an X-spermatozoon results in female descendants.

On the issue how to increase the probability to procreate male or female descendants, a number of household remedies exist worldwide, concerning especially the timing of sexual act between man and woman and/or the position meanwhile.

To be mentioned in this context are for example the so-called STORCH-parameters, wherein STORCH is composed of the initial letters of five parameters that are supposed to influence descendants sex:
  Position during sexual act (German: Stellung während des Geschlechtsakts)
  Timing: timing of sexual act in connection with the moon phases
  Orgasm-timing: timing of his or her orgasm
  Right nutrition/acid-base balance
  Chinese conception calendar
  Heat: temperature difference of male testicles While it is true that there are several promising statistics, concerning the mentioned parameters, especially regarding the Chinese conception calendar, it is also the case that the respective application of the procedure usually is time-consuming. Moreover, instructions for the procedure usually are equipped with significant space for interpretation.

In the course of artificial insemination there are further opportunities and in various countries sex-selection is permitted in the case of in vitro fertilisation. Concerning the treatment of a sample for in vitro fertilisation several procedures are known, for example from WO 02/052244 A1, which are intended to ensure separation of X- and Y-spermatozoa.

It is the object of the invention to provide a device which allows enrichment of X- and/or Y- chromosome-bearing spermatozoa, but at the same time does neither make high technical or financial demands nor is its handling very cumbersome for the user.

According to the invention, this object is solved by a device comprising a selectively permeable separating wall with the characteristics of independent claim 1, a selectively permeable separating wall with the characteristics of independent claim 10 as well as by a kit with the characteristics of independent claim 11. Preferred embodiments of the device and the kit are the subject to independent claims 2 to 9 and 12. The wording of all claims is hereby incorporated by reference into the description.

According to a first aspect, a device for insertion into a vaginal passage of a user or for accomodation of a penis during coitus is created, comprising a selectively permeable separating wall for the enrichment of X-chromosome-bearing spermatozoa or Y-chromosome-bearing spermatozoa, wherein the separating wall shows increased permeability for X-chromosome-bearing spermatozoa or Y-chromosome-bearing spermatozoa.

In connection with the application, a separating wall is referred to as selectively permeable if it shows an increased permeability for X-chromosome-bearing spermatozoa or Y-chromosome-bearing spermatozoa, while spermatozoa as bearers of the other type of chromosome are held back. There, the selectively permeable separating wall serves the enrichment of X-chromosome-bearing spermatozoa or Y-chromosome-bearing spermatozoa downstream of the separating wall.

The device is designed in such a way that it can be inserted into the vaginal passage of a user or accomodate a penis during coitus. In other words, the device is designed like a well-known barrier contraceptive, such as a pessary or a condom, and is handled in a similar way. In connection with the application, all products are generally called pessary, which are inserted into the vagina or are put on the cervix. A special type of a pessary is the diaphragm.

The selectively permeable separating wall preferably serves for modification of the ejaculate on the way to the cervix. The modification is, that the ejaculate or at least a part of the ejaculate, which passes through the selectively permeable separating wall, after the passage through the separating wall shows more, preferably only X- or Y-spermatozoa, while the other type of spermatozoa is held back at the separating wall.

As already indicated, mammalian sperm generally contains approximately the same number of X- and Y-spermatozoa. Due to an ejaculate modified with the help of the selectively permeable separating wall, the probability to achieve male (enrichment of Y-spermatozoa after the passage through the separating wall) or female (enrichment of X-spermatozoa after the passage through the separating wall) descendants can be increased.

According to an embodiment of the application, the selectively permeable separating wall shows pores or is designed as a sieve or mesh, wherein the size of the pores or the meshes of the selectively permeable separating wall is adapted to the size of the Y-chromosome-bearing spermatozoa, so that the selectively permeable separating wall shows an increased permeability for Y-chromosome-bearing spermatozoa.

In other words, the size of the pores or meshes of the selectively permeable separating wall is adapted to the size of the Y-spermatozoa, so that they can pass through the separating wall. In this way, an enrichment of Y-spermatozoa at the filtrate side and an enrichment of X-spermatozoa at the unfiltrate side is achieved. Those at least partially or completely separated X- and Y-spermatozoa might then be used for fertilisation or—especially when using a device covering a penis—be frozen for later use.

The separating effect of a corresponding selectively permeable separating wall is based on the surprising finding, that X- and Y-spermatozoa can at least partially be separated solely on the basis of their size. The separating wall according to the invention there acts as a kind of filter which, depending on the chosen pore size or mesh size at least partially, preferably completely, is retaining the X-chromosome-bearing spermatozoa (unfiltrate side) or is allowing a pass through of the Y-chromosome-bearing spermatozoa (filtrate side).

There is a measurable difference in size between X- and Y-spermatozoa in the micrometer range. Thus, an Y-spermatozoon has an average head circumference of 14.73 µm with a standard deviation value of 1.07 µm. An X-spermatozoon however shows an average head circumference of 15.26 µm with a standard deviation value of 1.17 µm. Therefore, the X-spermatozoon shows a head circumference which on average is about 530 nm taller. In terms of statistical evaluation, this difference is highly significant, i.e. the error probability p is less than 1% (p<0.001).

With particular advantage the selectively permeable separating wall is not only restricted to the use in human sperm or human spermatozoa but can also be applied to every kind of mammalian sperm, especially with the existence of a size difference between X-chromosome and Y-chromosome-bearing spermatozoa.

In advantageous embodiments, the selective permeable separating wall has pores with a nominal pore size in a range between approx. 3.800 µm and approx. 4.900 µm, preferably in a range between approx. µm 3.800 and approx. 4.500 µm, particularly in a range between approx. 3.900 µm and approx. 4.000 µm. In one embodiment, the pores are generated due to the porosity of a porous material used. In other embodiments, the pores are introduced into a non-porous material, particularly by laser cut, laser drilling, etching or the like. In one embodiment, the pores are shaped irregularly. In this case, the diameter of a circle covering the pore is called the pore size. Porous materials usually show pores of different pore sizes. The distribution of a materials pore sizes is called pore size distribution. The maximum in the pore size distribution is defined as the nominal pore size within the meaning of the application. In the case of a (hypothetic) circular pore with a nominal pore size of 4.900 µm, the pore openings circumference is about 15.394 µm.

According to the invention, in this context and in connection with all following information on nominal pore sizes, it is preferred that between 50 and 100%, particularly preferred between 60 and 99%, especially between 70 and 95% of all pores of the separating wall have the specified nominal pore size or at least fall below it.

In particular, the separating wall preferably has pores with a pore size D90 in a range between approx. 3.800 µm and approx. 4.900 µm, preferably in a range between approx. 3.800 µm and approx. 4.500 µm, particularly in a range between approx. 3.900 µm and approx. 4.000 µm. In connection with the application, that pore size is referred to as pore size D90, at which 90% of the materials pore volume have a pore size smaller than the pore size D90.

A materials pore size distribution can be determined by mercury porosimetry and/or gas adsorption. These methods are generally known to the specialist and described for example in the relevant standards ISO 15901-1 EN, ISO 15901-2 EN, ISO 15901-3 EN as well as DIN 66133, DIN 66134 and DIN 66135. Alternatively, a determination is performed by scanning electron microscopy, permeability measurements (gel-permeation-chromatography) and bubble point test.

In a different embodiment, the separating wall is designed as fabric or sieve with meshes, wherein the meshes have a mesh opening in a range between approx. 3.800 µm and approx. 4.900 µm, preferably in a range between approx. 3.800 µm and approx. 4.500 µm, particularly in a range between approx. 3.900 µm and approx. 4.000 µm. In this connection, the length of diagonal of a rectangular mesh is termed mesh opening. A determination is performed for example by scanning electron microscopy.

A separating wall according to the invention preferably has a statistical number of pores per unit of area between 10000 $mm^{-2}$ and 50000 $mm^{-2}$, preferably 15000 $mm^{-2}$ and 40000 $mm^{-2}$, particularly 20000 $mm^{-2}$ and 30000 $mm^{-2}$.

Experiments with a semen sample showed that with a nominal pore size of 4.773 µm, i.e. with a (hypothetic) pore with a circular cross-section and a pore openings circumference of approx. 14.995 µm, after passage through the selectively permeable separating wall 59.8% of Y-spermatozoa and 41.2% of X-spermatozoa exist in the remaining sample volume at the filtrate side. Thus, although the total sperm count was roughly halved, yet the received ratio of 59.8% Y-spermatozoa to 41.2% X-spermatozoa corresponds to an approx. 23% higher probability of a boy birth, on the assumption of an ideal initial composition of the semen sample of 50.0% Y-spermatozoa and 50.0% X-spermatozoa and thus a corresponding probability of 50% for a boy birth.

Considering the fact that on average, male ejaculate contains approx. $5 \times 10^8$ X- and Y-spermatozoa at the ratio of 1 to 1, after the described passage through a separating wall according to the invention with a nominal pore size of 4.773 µm there would still be approx. $2.5 \times 10^8$ spermatozoa available for a fertilisation.

During the passage of a semen sample through a separating wall according to the invention with a nominal pore size of only 3.937 µm, i.e. with a (hypothetic) pore with a circular cross-section and a pore openings circumference of approx. 12.368 µm, 1.37% Y-spermatozoa and 0.68% X-spermatozoa could be preserved on the filtrate side. At an initial average of $5 \times 10^8$ spermatozoa, this corresponds to still about 1% of the spermatozoa initially present in the sample. Under the same assumptions concerning the semen samples initial composition an about 51% higher probability for a boy birth results from the received ratio of 1.37% Y- to 0.68% X-spermatozoa with a number of spermatozoa of about $1 \times 10^7$ available for fertilisation.

Therefore, due to the permeability for Y-spermatozoa, which is shown by the selectively permeable separating wall with the above-mentioned preferred pore-sizes or mesh sizes, the probability for a boy birth can be increased preferably about more than 15%, particularly preferred 25%, especially 50%, if a sample received after the passage through the separating wall, enriched with Y-spermatozoa, is used for a fertilisation.

For the production of the separating wall, different biocompatible materials are conceivable, which preferably do not support adhesion or adherence of spermatozoa. As an ejaculate normally also contains proteinaceous substances to a significant extent, the material preferably shows protein repelling characteristics. In this way, unintended clogging of the pores or meshes can at least be avoided in parts.

The selection of a suitable material mainly depends on the embodiment of the device and how it is to be used. It is also conceivable that the separating wall is formed partially rigid, for example made of a ceramic material, wherein the device preferably shows additional areas that increase a wearing comfort.

Suitable materials are generally known to the person skilled in the art. On the free market, there is a great number of filtration materials, particularly for the life science sector, that are generally suited for the production of a selectively permeable separating wall according to the invention. The advantage of using such materials is that they normally already went through medical authorisation procedures and are classified as harmless and/or biocompatible.

Preferably, the selectively permeable separating wall is made of a polymer, chosen from the group comprising rubber, polylactid, cellulose, cellulose acetate, cellulose nitrate, polyethylene, polypropylene, polyurethane, polyisoprene, polytetrafluoroethylene, polyvinyl chloride, polyamide, polycarbonate, polyvinylidene fluoride, polyethersulfone, polysiloxane and combinations of them and/or is designed as an Anopore™-membrane.

According to another embodiment, the selectively permeable separating wall is at least on one side provided with a coating, particularly a basic coating.

In doing so, the basic coating is preferably applied to the filtrate side of the separating wall, thus on the side which does not get in touch with the ejaculate at first. Male sperm generally has a low pH value (7.2-7.8). By using a basic coating on the filtrate side of the separating wall, migration tendencies of spermatozoa on the unfiltrate side through the pores in direction of the filtrate side can be increased with particular advantage, if the filtration is carried out against an acidity gradient. An acidity gradient occures for example if acidic environment is dominant in the immediate surrounding of the separating walls filtrate side, while on the ulfiltrate side, a basic milieu exists due to the basic semen sample. In this case, the basic coating on the filtrate side leads to a compensation of the pH value in close proximity to the filtrate side, so that the migration speed of the spermatozoa in the direction of the acidic environment is increased. In one embodiment, the coating thereby is chosen in such a way, that the separating wall shows an increased permeability for X-chromosome-bearing spermatozoa.

Furthermore, an embodiment in which the coating on the filtrate side is provided with chemical attractants for spermatozoa (chemotaxis) is conceivable. Such attractants are known. It can for example be the same attractants secreted by an egg cell during the process of fertilisation for pointing the way to the spermatozoa (cyclical nucleotides, cAMP or cGMP).

Furthermore, the separating wall can at least on one side be enriched, impregnated or equipped with bactericides, deodorants or lubricants. Also it can be enriched, impregnated or equipped with several pharmacological compounds such as hormones and derivates. Methods of combination with medications, hormones or other pharmacological compounds are generally known to persons skilled in the art.

According to a particularly preferred embodiment, the selectively permeable separating wall is shaped as a component of a condom, a diaphragm or a pessary.

For the purpose of production of such a condom, pessary or diaphragm, the selectively permeable separating wall in advantageous embodiments is at first available in the shape of a foil or membranous in the thickness and/or shape common for a condom or a diaphragm. Materials, offering themselves for this purpose are those materials usually used for condoms (e.g. polyisoprene, polyethylene, polyurethane) and diaphragms (e.g. silicone, polyimide). In the production process a part of the condom, especially in the area of the sperm reservoir, or a part of the diaphragm, especially in the area of the area centroid, can then be replaced by the selectively permeable separating wall. The connection of the materials for example is made by gluing or welding.

Alternatively, the selectively permeable separating wall is designed as a condom, pessary or diaphragm. According to this embodiment, both the condom and the diaphragm as a whole are made of a material also acting as a separating wall. A usually cumbersome gluing or welding can then be omitted. There in one embodiment, strengthened areas, inserts or such are provided, which for example act as clamping ring for a diaphragm.

If the selectively permeable separating wall is shaped as a condom, it can further be preferred that the outer surface of the condom (equal to the filtrate side) is equipped with a basic coating. In the female vaginal area there usually exists acidic environment, so that the basic coating as described above effects a compensation of the pH-value and therefore supports the migration of the spermatozoa in the condom in the direction of the filtrate side.

If the selectively permeable separating wall is shaped as a pessary or diaphragm, provision is particularly made for the side that faces the cervix after the placement of the pessary or diaphragm (equal to the filtrate side) being provided with a basic coating. Thus, migration tendency of the spermatozoa through the selectively permeable separating wall in the direction of the cervix can be increased.

According to a second aspect, a selectively permeable separating wall for a device for insertion into a vaginal passage of a user or for accommodation of a penis during coitus is provided. There, the selectively permeable separating wall is combinable with and/or applicable in the device before usage. For example, in one embodiment, the device comprises a vaginal ring, to which a selectively permeable separating wall can be exchangeably attached.

Another embodiment of the invention is a kit for the enrichment of X-chromosome or Y-chromosome-bearing spermatozoa, comprising a device with a selectively permeable separating wall according to the explanations above and at least a lubricant.

Preferably, the kit comprises a selectively permeable separating wall designed as a condom or a diaphragm and/or as a integral part of a condom or a diaphragm, wherein the individual components of the kit are packaged preferably spatially separated from one another and especially sterile.

In another embodiment of the kit according to the invention, the kit, in addition to or instead of the lubricant, comprises a substance for the generation of a basic coating on the selectively permeable separating wall. The substance might preferably also function as a lubricant, so that the existence of a separate lubricant is not necessary.

According to a preferred embodiment, the kit comprises a selectively permeable separating wall for the usage with a device designed as a condom and/or designed as a diaphragm as well as a lubricant and a substance for the generation of a basic coating as described above.

Further advantages of the invention result from the dependant claims and from the following description of the embodiment examples of the invention which are pictured schematically in the drawings. In the drawings, uniform reference signs are used for equal or similar component parts. Characteristics that are described or pictured as a part of an embodiment, might also be used in a different embodiment example in order to get another embodiment of the invention.

Figure 2:
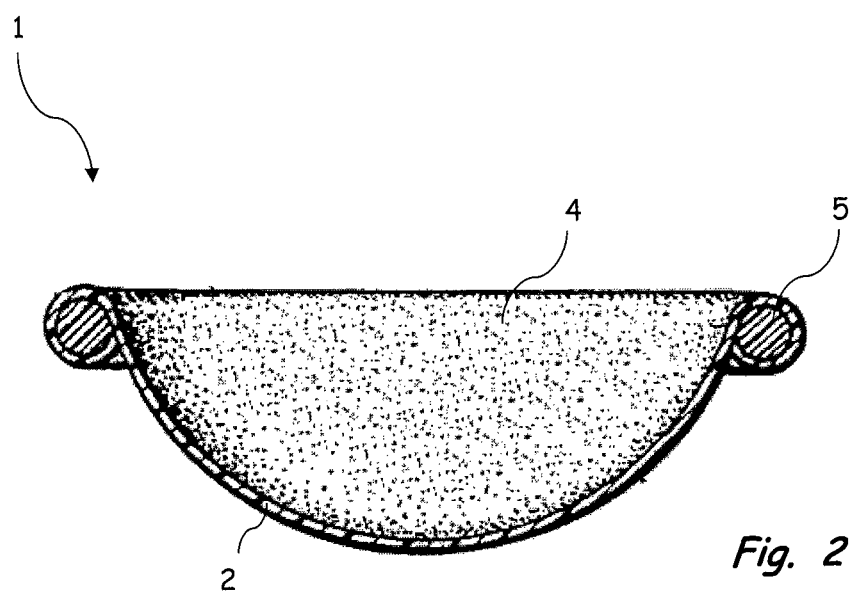

In the drawings are shown:

FIG. 1 a perspective presentation of an embodiment of a device according to the invention in the shape of a diaphragm FIG. 2 a cross section of the diaphragm from FIG. 1

Figure 3:
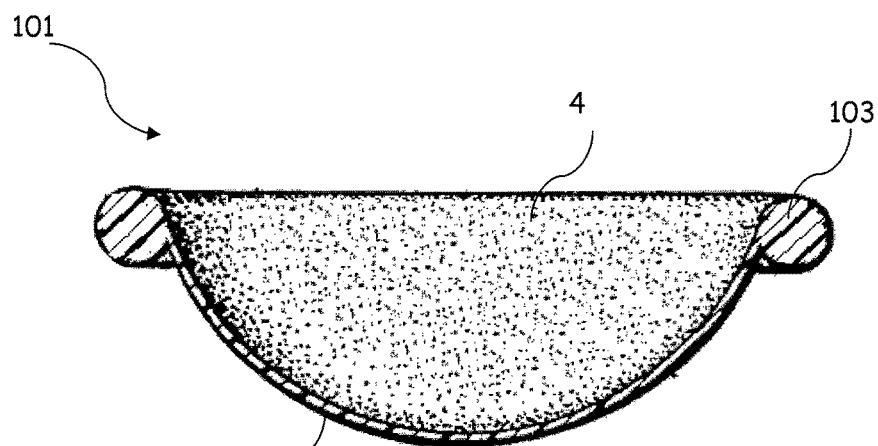

FIG. 3 a cross section of a diaphragm similar to FIG. 1

Figure 4:
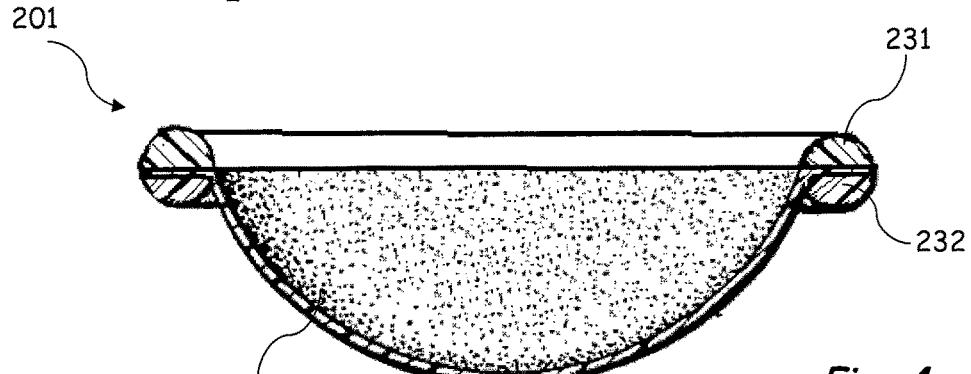
Figure 5:
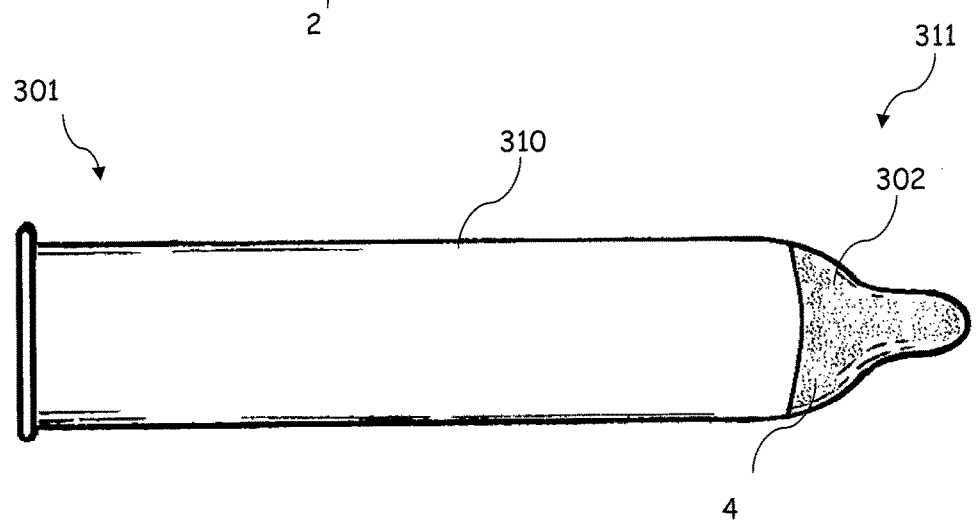

FIG. 4 a cross section of a diaphragm similar to FIG. 1 with an exchangeably accommodated separating wall and FIG. 5 a profile of an embodiment of a device according to the invention designed as a condom.

FIGS. 1 and 2 show a device 1, designed as a dome-shaped diaphragm, comprising a selectively permeable separating wall 2 in a perspective presentation and a cross section, respectively.

The separating wall 2 is made as an elastic membrane, for example made of silicone or polyamide. Furthermore, the diaphragm comprises a dimensionally stable, elastic ring 3, which serves for the insertion of the diaphragm into a vagina and due to which it is guaranteed, that the shape of the diaphragm is preserved also after insertion into the body.

The selectively permeable separating wall 2 shows schematically, not scaled pictured pores 4 with a nominal pore size of 4.773 μm. Due to the choice of the pore size, the selectively permeable separating wall shows an increased permeability for Y-chromosome-bearing spermatozoa.

FIG. 3 shows an alternative embodiment of a device 101 designed as dome-shaped diaphragm comprising a selectively permeable separating wall 2 in a cross section. The design is similar to the FIGS. 1 and 2 and for equal designs uniform reference signs are used. Unlike the embodiment according to the FIGS. 1 and 2, the diaphragm according to FIG. 3 is made up as an integral part of one material, wherein a section 103 functions as an elastic ring element.

FIG. 4 shows another alternative embodiment of a device 101 designed as dome-shaped diaphragm, comprising a selectively permeable separating wall 2 in a cross section. Also the design according to FIG. 3 is similar to the FIGS. 1 and 2 and for equal designs uniform reference signs are used. Unlike the embodiment according to the FIGS. 1 and 2, the device 201 comprises a two-piece ring. The ring shows two ring elements 231, 232 connectable to each other, between which a selectively permeable separating wall 2 is accommodated exchangeably. Thereby, the ring, particularly its size and/or elasticity is individually customizable to a user. The selectively permeable separating wall 2 can thereby be designed in such a way, that it is suitable for different ring designs.

FIG. 5 shows a profile of a device 301 according to the invention designed as a condom with a selectively permeable membrane 302. The pictured condom shows a tubular area 310 and a sperm reservoir 311, wherein the area of the sperm reservoir 311 is made up of a selectively permeable separating wall 302. The connection of the separating wall 301 with the tubular area is preferably made by gluing or welding. In this process, it is possible to use a different material for the sperm reservoir 311 than for the tubular area.

The invention claimed is:

1. A method of increasing a probability to procreate male or female descendants, comprising partly or completely separating X-chromosome-bearing spermatozoa and Y-chromosome-bearing spermatozoa using a device adapted for insertion into a vaginal passage or for accommodation of a penis during a coitus, said device comprising a selectively permeable separating wall having pores, wherein a size of the pores of the selectively permeable separating wall is adapted to a size of the Y-chromosome-bearing spermatozoa, so that the separating wall has an increased permeability for Y-chromosome-bearing spermatozoa.

2. The method according to claim 1, wherein the pores have a nominal pore size in a range between approximately 3.800 μm and approximately 4.900 μm.

3. The method according to claim 1, wherein the selectively permeable separating wall has a statistical average of pores per unit area between 10000 $mm^2$ and 50000 $mm^2$.

4. The method according to claim 1, wherein the selectively permeable separating wall at least partially is made of a polymer, selected from the group comprising rubber, polylactid, cellulose, cellulose acetate, cellulose nitrate, polyethylene, polypropylene, polyurethane, polyisoprene, polytetrafluoroethylene, polyvinyl chloride, polyamide, polycarbonate, polyvinylidene fluoride, polyethersulfone, polysiloxane and combinations thereof.

5. The method according to claim 1, wherein the selectively permeable separating wall is at least on one side provided with an alkaline coating.

6. The method according to claim 1, further providing a substance for a generation of an alkaline coating on the separating wall.

7. The method according to claim 1, wherein the pores have a nominal pore size in a range between approximately 3.800 μm and approximately 4.500 μm.

8. The method according to claim 1, wherein the pores have a nominal pore size in a range between approximately 3.900 μm and approximately 4.000 μm.

9. The method according to claim 1, wherein the selectively permeable separating wall has a statistical average of pores per unit area between 15000 $mm^2$ and 40000 $mm^2$.

10. The method according to claim 1, wherein the selectively permeable separating wall has a statistical average of pores per unit area between 20000 $mm^2$ and 30000 $mm^2$.

11. A method of increasing a probability to procreate male or female descendants, comprising partly or completely separating X-chromosome-bearing spermatozoa and Y-chromosome-bearing spermatozoa using a device adapted for insertion into a vaginal passage or for accommodation of a penis during a coitus, said device comprising a selectively permeable separating wall having mesh fabric with mesh openings, wherein a size of the mesh openings is adapted to a size of the Y-chromosome-bearing spermatozoa, so that the selectively permeable separating wall has an increased permeability for Y-chromosome-bearing spermatozoa.

12. The method according to claim 11, wherein the size of the mesh openings is in a range between approximately 3.800 μm and approximately 4.900 μm.

13. The method according to claim 11, wherein the size of the mesh openings is in a range between approximately 3.800 μm and approximately 4.500 μm.

14. The method according to claim 11, wherein the size of the mesh openings is in a range between approximately 3.900 μm and approximately 4.000 μm.

15. The method according to claim 11, wherein the selectively permeable separating wall has a statistical average of pores per unit area between 10000 $mm^2$ and 50000 $mm^2$.

16. The method according to claim 11, wherein the selectively permeable separating wall at least partially is made of a polymer, selected from the group comprising rubber, polylactid, cellulose, cellulose acetate, cellulose nitrate, polyethylene, polypropylene, polyurethane, polyisoprene, polytetrafluoroethylene, polyvinyl chloride, polyamide, polycarbonate, polyvinylidene fluoride, polyethersulfone, polysiloxane and combinations thereof.

17. The method according to claim 11, wherein the selectively permeable separating wall is at least on one side provided with an alkaline coating.

18. The method according to claim 11, further providing a substance for a generation of an alkaline coating on the separating wall.

19. The method according to claim 11, wherein the selectively permeable separating wall has a statistical average of pores per unit area between 15000 mm$^2$ and 40000 mm$^2$.

20. The method according to claim 11, wherein the selectively permeable separating wall has a statistical average of pores per unit area between 20000 mm$^2$ and 30000 mm$^2$.

* * * * *